(12) United States Patent
Insepov et al.

(10) Patent No.: US 7,651,673 B1
(45) Date of Patent: Jan. 26, 2010

(54) METHOD AND SYSTEM FOR SMALL SCALE PUMPING

(75) Inventors: Zeke Insepov, Darien, IL (US); Ahmed Hassanein, Bolingbrook, IL (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 12/467,987

(22) Filed: May 18, 2009

Related U.S. Application Data

(63) Continuation-in-part of application No. 11/566,362, filed on Dec. 4, 2006.

(60) Provisional application No. 61/054,896, filed on May 21, 2008.

(51) Int. Cl.
*D01F 9/12* (2006.01)
(52) U.S. Cl. .................. 423/447.1; 204/157.62
(58) Field of Classification Search .............. 423/447.1; 204/157.62
See application file for complete search history.

(56) References Cited

OTHER PUBLICATIONS

Yoon et al, Sound Wave Poropagation, J. App. Physics, 2003, 93, 8, 4801-4806.*
Insepov et al, Nanopumping, Nano Letters, 2006, 6,9, 1893-1895.*

* cited by examiner

*Primary Examiner*—Melvin C Mayes
*Assistant Examiner*—Bijay S Saha
(74) *Attorney, Agent, or Firm*—Mark C. Lang; Brian J. Lally; Paul A. Gottlieb

(57) ABSTRACT

The present invention relates generally to the field of small scale pumping and, more specifically, to a method and system for very small scale pumping media through microtubes. One preferred embodiment of the invention generally comprises: method for small scale pumping, comprising the following steps: providing one or more media; providing one or more microtubes, the one or more tubes having a first end and a second end, wherein said first end of one or more tubes is in contact with the media; and creating surface waves on the tubes, wherein at least a portion of the media is pumped through the tube.

18 Claims, 5 Drawing Sheets

METHOD AND SYSTEM FOR SMALL SCALE PUMPING

RELATION TO OTHER APPLICATIONS

This Non-Provisional Patent is related to and claim priority to U.S. Provisional Patent Application No. 61/054,896 filed May 21, 2008, the current application is also Continuation-In-Part Patent Application of U.S. Non-Provisional patent application Ser. No. 11/566,362 filed Dec. 4, 2006 both of which are hereby incorporated by reference in their entireties.

STATEMENT OF GOVERNMENTAL SUPPORT

This invention was made during work supported by the U.S. Department of Energy under Contract No. Contract No. DE-AC02-06CH11357. Therefore, the United States Government has certain rights to this invention.

FIELD OF INVENTION

The present invention relates generally to the field of very small scale pumping more specifically, to a method and system for pumping media through micro-tubes.

BACKGROUND OF INVENTION

The study of narrow channels has become a popular area of research since the discovery of carbon nanotubes by Sumio Ijima in 1991. Ijima found that carbon fibers, which were already known to exist, were in fact hollow. Part of the fullerene structural family (which also includes buckyballs), carbon nanotubes can be generally described as rolled-up sheets of graphite with diameters on the order of several nanometers (1 nm=$10^{-9}$ m). There are two common types of carbon nanotubes: single-walled carbon nanotubes and multi-walled carbon nanotubes. Single-walled carbon nanotubes consist of one rolled sheet of one-atom-thick graphite (called graphene). Multi-walled carbon nanotubes are made of concentric cylinders of graphene (e.g., a single-walled carbon nanotube within a larger single-walled carbon nanotube). Despite their small size, carbon nanotubes are known to exhibit remarkable strength and have other unexpected electrical and structural properties.

In recent years the study of fluid control in narrow channels has become a hot area of research. Current research has centered on microflow systems including liquid flows in narrow slit-pores, very thin liquid film on solid surfaces, flows in micropumps, microarrays and membranes. Although fluid flow dynamics in carbon nanotubes has been studied to some degree, research in this area has focused on: laser driven atomic transport using electric current which drives ions using drag forces (citation) and nano-pipette systems for dragging metal ions through a multi-walled CNT using electromigration forces. There is a need in the art for a new method of pumping non-ionic media on a nanoscale and micron scale.

Nanotubes have also been studied for their energy storage capabilities. Of particular importance is the issue of how to store and release hydrogen in a safe and practical manner. The energy storage capabilities of carbon nanotubes have been explored through the two forms of adsorption: chemisorption and physisorption. Adsorption, in general, is where a gas or liquid accumulates on the surface of a solid or liquid and forms a molecular or atomic film. Chemisorption is a form of adsorption where molecules attach to the surface of the carbon nanotube by forming a chemical bond. Physisorption is a form of adsorption where molecules adhere to the surface of the carbon nanotube only by weak intermolecular forces (Van der Waals forces). However, the chemisorption and physisorption methods of hydrogen storage are problematic because the release of hydrogen from the carbon nanotube structure is complicated. Proposed methods to release hydrogen from the carbon nanotube structure require very high temperatures and are thus unrealistic in application. There is a need in the art for a new hydrogen storage and release method and system.

A new method for storing and pumping media on a micro scale could have a significant effect on a wide range of technologies including but not limited to: direct methanol fuel cell development, hydrogen energetics, nano-robotics, nano-scale printing, atom optics, quantum computing, semiconductors, forensic and nucleotide analysis, chemical process control, cell biology, medical drug delivery, and molecular medicine.

BRIEF SUMMARY OF THE INVENTION

The present invention is a method for pumping gaseous, liquid solid, or other media through sub-micron and micron size channels and tubes. One embodiment of the invention generally comprises the following steps: (1) providing a plurality of microtubes each tube having a first and second end with the first end in contact with a gaseous, liquid, or solid media; and (2) creating surface waves along the tubes which pumps media through the tube(s).

In an alternative embodiment, the tubes are filled (imbibition) before surface waves are created on the tubes.

DETAILED DESCRIPTION OF THE INVENTION

Figure 1A:
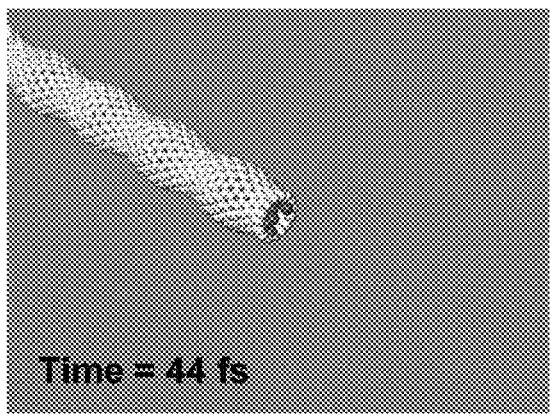
FIGS. 1A-1D illustrate the Molecular Dynamics simulation described below.
Figure 1B:
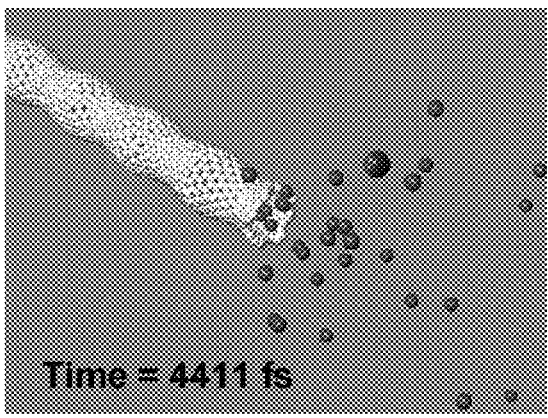
Figure 1C:
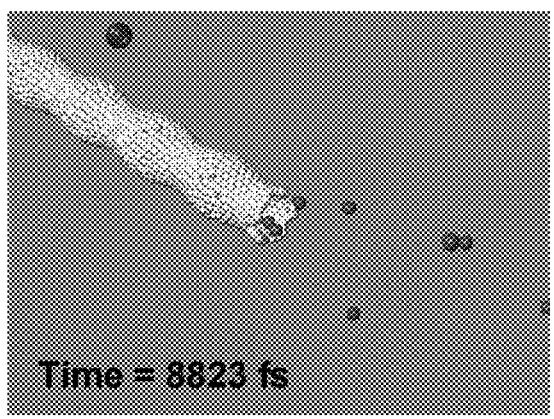
Figure 1D:
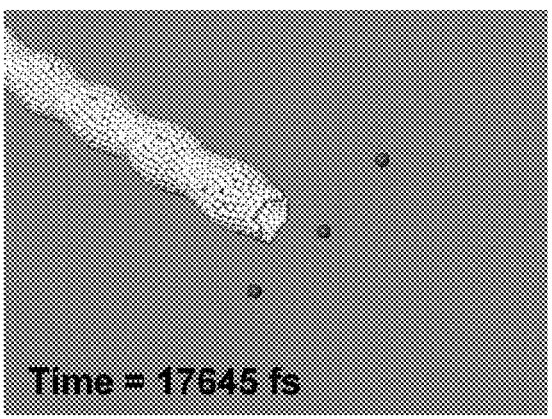

The present invention relates to a method for pumping media through small scale channels or tubes. More specifically, the present invention relates to a method of micro-pumping in which waves are produced at the surface of the tube(s) to propagate liquid, gases, or other media through the sub-micro- and micro size tube(s).

One preferred embodiment of the invented method of very small scale pumping generally comprises the following steps:
a. providing a media to be pumped;
b. providing a plurality of micro tubes, each tube having a first and second end with the first end in contact with said media;
c. creating surface waves along the tubes.

The surface waves transform the tubes into a micro-scale pump capable of pumping media. The driving force behind the pump is the friction between the media (i.e. gas, liquid) and the tube walls. As shown in FIGS. 1A-D gas atoms inside the tube move almost freely along ballistic trajectories when surface waves are created on the tubes. The gas atoms are easily accelerated to a very high axial velocity along the direction of the traveling wave. The increase in acceleration is a result of multiple synchronous collisions with the moving nanotube walls (resulting from the surface waves). The surface waves cause the media to be pumped through the tube in the direction of the traveling surface wave.

As noted in an alternate embodiment the tubes can be imbibed with media prior to the creation of surface waves on the tube(s).

Media

The media pumped through the tube can be virtually any media capable of being pumped through the chosen tubes. Preferably the media will have atoms being smaller than the diameter of the tube, preferably having a size of lest than ½ the diameter of the tube. The media can be a gas, liquid, solid, other media, or combinations thereof.

In one preferred nano-scale embodiment the media is comprised of atoms having individual masses less than that of a carbon atom, more preferably the media is comprised of hydrogen or helium gas, and even more preferably hydrogen gas.

In one preferred micron-scale embodiment the media is comprised of air or oxygen, and methanol fuel.

The tubes can be imbibed with the media prior/during pumping or the media can be drawn into the tube by a vacuum-like effect caused by the surface waves.

Microtubes

The microtubes of the present invention can be made of variety of materials known in the art capable of forming micron scale tubes including but not limited to various metals, metal alloys, ceramics, semiconductors, organics, composites and polymers. Preferred materials include but are not limited to: stainless steel, gold, titanium, nickel, iron, chromium, iron, tin, copper, palladium, platinum, alloys of these metals, silicon, silicon dioxide and polymers. See, also U.S. Pat. No. 7,334,499, incorporated by reference in its entirety.

In terms of size, there are several factors to consider in the context of the present invention. The microtubes can have a wide range of diameters. However, it is preferable to employ microtubes having diameters less than about 200 microns.

The length of the microtubes can be varied, however, as discussed below, the length of the tube affects the preferred frequencies of the waves. The tubes may be virtually any length, but the length will usually be dictated by the application for which the tubes will be used. A suitable range for the length of the microtube is generally less than about 2-5 inches. The length of the tube defines the resonant frequency of the pump.

In terms of arrangement, microtubes can be made or purchased in a variety of configurations including but not limited to: bundles, ropes, or arrays. A bundle of microtubes generally describes a grouping, in some fashion, of more than one microtubes. Microtubes can be made using a variety of techniques including those described in U.S. Pat. Nos. 7,344,499; 7,226,439; 6,334,856; 6,194,066; 6,663,820 and the publication High Strength Superelastic Ti—Ni Microtubes Fabricated by Sputter Deposition, Buenconsejo et al., Acta Materialia 56 (2008) 2063-2072; which are all hereby incorporated by reference in their entireties.

Bundles of microtubes can be aligned tubes (e.g., tube ropes) or microtubes arranged in a random configuration (e.g., crisscrossed in a straw-like mat). Ropes are bundles of tubes that are packed together parallel to one another in an orderly fashion. Arrays are groupings of tubes where the tubes have been grown in a particular formation (usually not touching one other) to serve a particular purpose. For example, a 5 tube by 5 tube square array where there is a uniform space between all the tubes.

The present invention is applicable to a single microtube; however, it can be applied to a plurality of tubes. A plurality of micro or nanotubes will have similar pumping effects. The number of tubes required will be determined by the specific application. For example, a larger quantity of tubes may be required for a hydrogen storage application than for a more exact application, such as medical drug delivery or small scale robotics. The tubes also have the option of being filled (imbibition) with a media.

Nanotubes

Nanotubes can also be used, in place of or in addition to microtubes. When employing nanotubes and when working on the nanoscale certain factors need to be considered as described below. Suitable nanotubes are carbon nanotubes. Depending on the application, carbon nanotubes may be needed in different diameters, lengths and configurations. The carbon nanotubes (CN) can be produced the using techniques well-known in the art (e.g., U.S. Pat. No. 6,900,580, U.S. Pat. No. 6,939,525, U.S. Pat. No. 7,008,605) or purchased from a manufacturer. Several manufacturers of carbon nanotubes that may be suited for the present invention are: NanoLab, Inc., Newton, Mass.; Cheap Tubes, Inc., Brattleboro, Vt.; and Helix Material Solutions, Richardson, Tex. All three of these manufacturers are able to produce carbon nanotubes in various sizes and arrangements. When possible one may purchase carbon nanotubes prefilled with a desired media.

In terms of size, there are several factors to consider in the context of the present invention. The carbon nanotubes used in the present invention can have a wide range of diameters. However, it is preferable to employ carbon nanotubes having diameters between about 1 and 200 nm. The diameters of nanotube are limited to the strength of the tube as the nanotubes with large diameters are not normally strong enough to be considered as a future nanopump media.

The length of the carbon nanotubes can be varied, however, as discussed below, the length of the nanotube may affect the preferred frequencies of the waves. The carbon nanotubes may be any length, but the length will usually be dictated by the application for which the carbon nanotubes will be used A suitable range for the length of the nanotube is between about 10 nm-1000 nm, preferably between about 10 nm and 200 nanometers. The length of the nanotube defines the resonant frequency of the nanopump. If the length is too large, e.g. larger than a few mm, it will be very difficult to stabilize the nanotube for using it as a nanopump. The nanopump effect may not be existed at such long nanotube. Therefore, we limit the overall length for a stable nanopumping effect to a few hundred microns.

For larger diameters, the carbon nanotubes may preferably be multi-walled carbon nanotubes as multi-walled carbon nanotubes tend to be more structurally stable.

Another characteristic of carbon nanotubes, the chiral vector, need not be any specific pair of indices. The chiral vector (n, m) of a carbon nanotube represents the way in which the graphene sheet is rolled to form the carbon nanotube. There are three types of chiral vectors: zigzag (if either n=0 or m=0, and the chiral angle is 0°), armchair (if n=m, and the chiral angle is 30°), and chiral (all other vectors with chiral angle between 0° and 30°). In the present invention, the chiral vector, sometimes also referred to as simply "chirality," does not appear to affect the method and, therefore, can have any value.

In terms of arrangement, carbon nanotubes can be made or purchased in a variety of configurations including but not limited to: bundles, ropes, or arrays. A bundle of carbon nanotubes generally describes a grouping, in some fashion, of more than one carbon nanotube. Bundles of carbon nanotubes can be aligned carbon nanotubes (e.g., carbon nanotube ropes) or carbon nanotubes arranged in a random configuration (e.g., crisscrossed in a straw-like mat). Ropes are bundles of carbon nanotubes that are packed together parallel to one another in an orderly fashion. Carbon nanotubes naturally form ropes and are held in such a formation by Van der Waals forces (weak intermolecular forces). Arrays are groupings of carbon nanotubes where the carbon nanotubes have been grown in a particular formation (usually not touching one other) to serve a particular purpose. For example, a 5 carbon nanotube by 5 carbon nanotube square array where there is 5 nm of space between all carbon nanotubes. In arrays, the carbon nanotubes are typically grown on a substrate to which they are then attached at one end.

The present invention is applicable to a single carbon nanotube; however, it can be applied to a plurality of nanotubes. A plurality of nanotubes will have similar nano-pumping effects. The number of nanotubes required will be determined by the specific application. For example, a larger quantity of carbon nanotubes may be required for a hydrogen storage application than for a more exact application, such as medical drug delivery or nano-robotics. Carbon nanotubes also have the option of being filled (imbibition) with a media.

Typically, carbon nanotubes are capped at each end with half of a fullerene (buckyball). However, it is also possible for carbon nanotubes to be open at both ends or capped on just one end. Depending on the application, the carbon nanotube might have any of the above characteristics/configurations.

Surface Waves on the Tubes

A salient aspect of the invention is the creation of surface waves on the surface of the tubes. The surface waves are preferably transverse longitudinal waves. The waves are more preferably Raleigh waves.

There at least two known methods of creating surface waves on small scale tubes. One method uses short laser pulses to generate thermo-acoustic waves on tubes as described by K. L. Telschow, V. A. Deason, D. L. Cottle, J. D. Larson III, UHF Acoustic Microscopic Imaging of Resonator Motion, *IEEE* 2000 *Ultrasonics Symposium in Puerto Rico*, Oct. 22-25, 2000, which is hereby incorporated by reference in its entirety.

Another way is to send ultra-sound waves through a liquid or dense gaseous media to tubes as described by I. A. Viktorov, *Rayleigh and Lamb Waves: Physical Theory and Applications* (Plenum, New York, 1967), which is hereby incorporated by reference in its entirety.

Both techniques use traveling waves to activate Rayleigh transverse surface waves on the surface of small scale tubes. See, J. Yoon et al, Sound Wave Propagation in Multi-Wall Carbon Nanotubes, J. Appl. Phys., Vol. 93, No. 8, 2003; Q. Wang, Wave propagation in carbon nanotubes via nonlocal continuum mechanics, J. Appl. Phys., Vol. 98, 124301, 2005; T. Natsuki et al., Wave propagation of carbon nanotubes embedded in an elastic medium, J. App. Phys. Vol. 97, 044307, 2005; V. N. Popov et al, Elastic properties of single-walled carbon nanotubes, Physical Review B, Vol. 61, No. 4, 2000; all of which are hereby incorporated by reference in their entireties. Whatever technique is used it should be used to a sufficient degree to induce surface waves on the tubes of the wave type and frequency described herein.

The induced surface waves can have a wide range of frequencies. The preferred frequency is dependent on the length of the tube being used as discussed in detail below. For shorter nanoscale tubes, the preferred range is generally less than about 60 THz, and more preferably between about 10 and 60 THz. However, for longer nanotubes the frequency could be much smaller. At the micron scale the frequency would be smaller yet. As discussed there is a strong relationship between length of the tube and frequency sufficient to create such waves.

Rayleigh transverse surface waves are activated when a longitudinal wave traveling in a liquid or gas impinges on a solid surface at an incident angle equal to the Rayleigh angle $\theta$ (where $\theta = \text{Arcsine}(C_p/C_s)$, $C_p$ is the velocity of the incident wave and $C_s$ is the velocity of the surface wave in the material). See Viktorov, supra.

The surface waves transform the tubes into micro and/or nano-scale pumps capable of pumping the media. The driving force behind the pump is the friction between the media (i.e. gas, liquid) and the tube walls which pumps and/or flows the media in the direction of the traveling surface wave. As shown in FIGS. 1A-D gas atoms inside the tube move almost freely along ballistic trajectories when surface waves are created on the tubes. The gas atoms are easily accelerated to a very high axial velocity along the direction of the traveling wave. The increase in acceleration is a result of multiple synchronous physical collisions with the moving tube walls (resulting from the surface waves).

Imbibition of Tubes

The tubes can be imbibed with one or more media prior to the commencement of the pumping process. Such imbibition might be preferable when using the invented method for certain applications including but not limited to: storage uses and delivery methods. For example, the tubes could be imbibed with a biologically active compound such as a pharmaceutical or an energy media such as hydrogen, and then released using the invented pumping process.

Imbibition is the term used to describe a process for filling tubes. One imbibition method is taught by Supple et al., which is hereby incorporated by reference in its entirety. (See, S. Supple and N. Quirke, Rapid Imbibition of Fluids in Carbon Nanotubes, *Phys. Rev. Lett.* 90, 214501 (2003), see, also P. M. Ajayan, S. Iijima, "Capillarity-induced filling of carbon nanotubes". Nature 361, 333-334 (1993); E. Dujardin, T. W. Ebbesen, H. Hiura, K. Tanigaki, "Capillarity and wetting of carbon nanotubes". Science 265, 1850-1852 (1994); M. R. Pederson, J. Q. Broughton, "Nanocapillarity in fullerene tubules". Phys. Rev. Lett. 69, 2689-2692 (1992); B. C. Regan, S. Alon, R. O. Ritchie, U. Dahmen, A. Zettl, "Carbon nanotubes as nanoscale mass conveyors", *Nature* 428, 924-927 (29 Apr. 2004) which are also incorporated by reference in their entireties.

Results

Several simulations were performed using Molecular Dynamics (MD), a type of molecular modeling based on molecular mechanics. The input structure used for the MD simulations came from coordinates of the zigzag nanotube carbon atoms that were generated.

Tersoff and Brenner interaction potentials were used to describe the carbon-carbon interactions of the nanotube. The Tersoff potential is a three-body potential function explicitly including an angular contribution to force that is widely used in MD for silicon, carbon and others. J. Tersoff, Empirical Interatomic Potential for Carbon, With Applications to Amorphous Carbon, *Phys. Rev. Lett.* 61, 2879-2882 (1988); J. Tersoff, New Empirical Approach for the Structure and Energy of Covalent Systems, *Phys. Rev. B* 37, 6991-7000 (1988). The Brenner potential is similar to the Tersoff potential but also includes special parameterizations for carbon and hydrocarbon systems. D. Brenner, Empirical Potential for Hydrocarbons for Use in Simulating the Chemical Vapor Deposition of Diamond Films, *Phys. Rev. B* 42, 9458-9471 (1990).

The overall system was brought into equilibrium at room temperature and Rayleigh transverse surface waves were created by sending traveling waves with a frequency between about $10^6$-$10^{13}$ Hz along the tube. The Rayleigh surface waves had a phase velocity of about 22 km/s. Displacement of the carbon in the tubes was perpendicular to the axial direction of wave propagation. In other words, the tube vibrations were in the radial directions with amplitudes in the interval of 1-5% of the tube radii.

Gas atoms in quantities of either 128 or 256 atoms were placed inside the tube by applying a traveling wave along the tube surface. Four types of gas atoms were used. The MD simulation takes into account the interaction between the gas atoms and the tube and how that interaction affects gas flow. The following tube chiralities were tested: (5×0), (15×0), (10×0), and (15×15). The total length of the tube was equal to 100 Å (10 nm) and the diameter was between 10 to 20 Å (1-2 nm). Depending on the number of gas atoms inside the carbon tube, the real simulation time was about 35 ps.

The simulation results in FIGS. 1A-1D show that the gas atoms inside the carbon nanotube move almost freely along ballistic trajectories. Also, the gas atoms are easily accelerated to a very high axial velocity along the direction of the traveling wave. The increase in acceleration is a result of multiple synchronous collisions with the moving nanotube walls (result of the surface waves). Specifically, FIGS. 1A-1D demonstrate the nano-pumping effect for 256 He (helium) atoms (shown by the dark grey small spheres) that were placed inside a carbon nanotube with a length of 100 Å (10 nm) and a diameter of 12 Å (1.2 nm). The carbon nanotube has a chirality of (15×0) and is made of 1410 carbon atoms. After the surface traveling was activated with a frequency of 10 THz and phase velocity of 22 km/s, the helium atoms began to move in the direction of the wave propagation (from left to right as in FIGS. 1A-1D). FIGS. 1A-1D display various instants in time during the simulation and the corresponding positions of the He atoms.

Length/Frequency

Figure 2A:
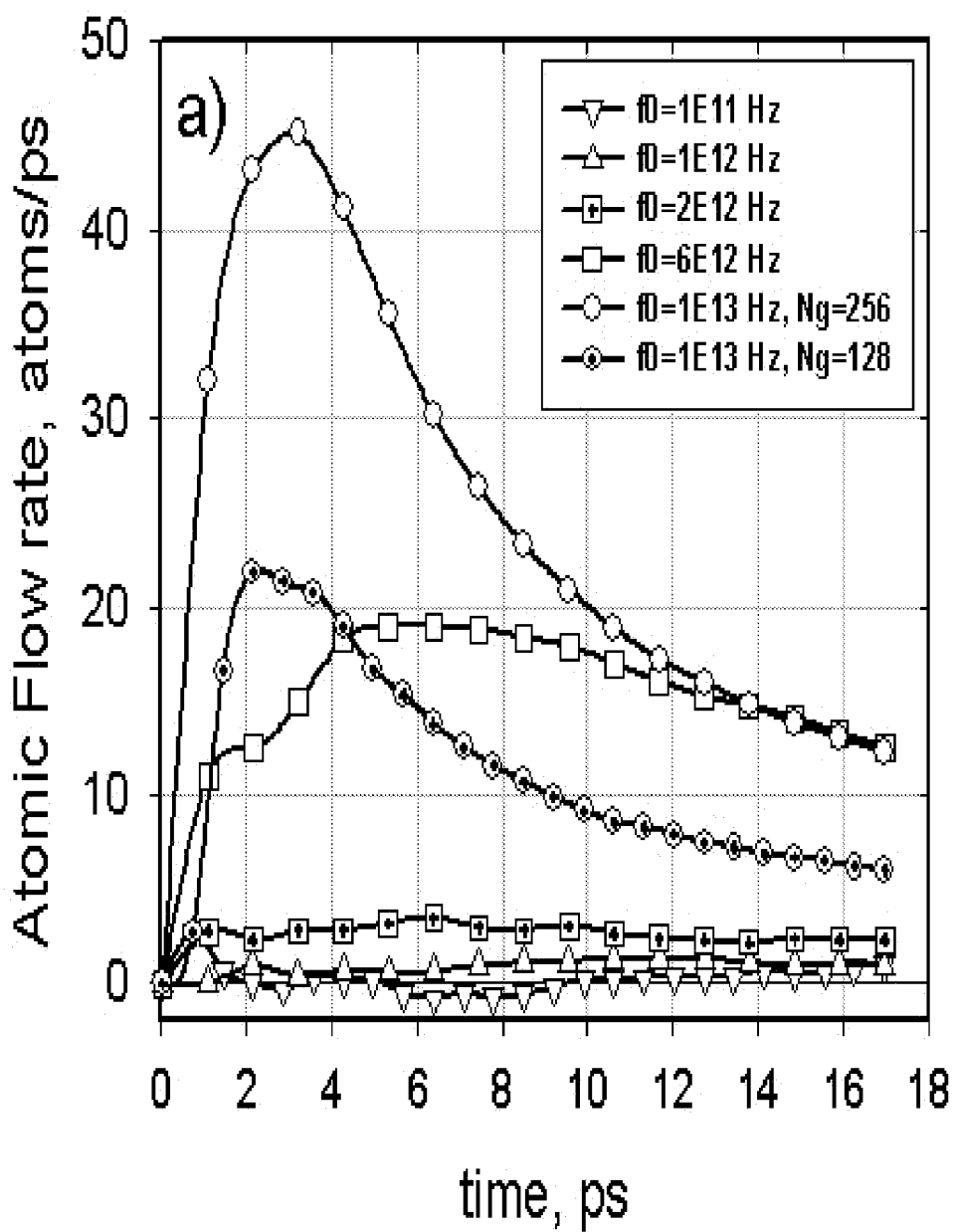
FIGS. 2A-2B are graphs displaying the time-dependence of the flow rate of the media through the small scale tubes, in this case nanotubes.

During the MD simulations of nano-tubes it was discovered that there was an important relationship between the length of small scale tubes and preferred frequency of the surface waves. During the MD simulations described above atomic fluxes were generated from the pumping effect for various frequencies of the surface waves for the gases initially at rest (velocity of zero) are shown in FIG. 2A. The total flux increases and then, after a few picoseconds, decreases because of the depletion of the gas atoms inside the nanotube.

Figure 2B:
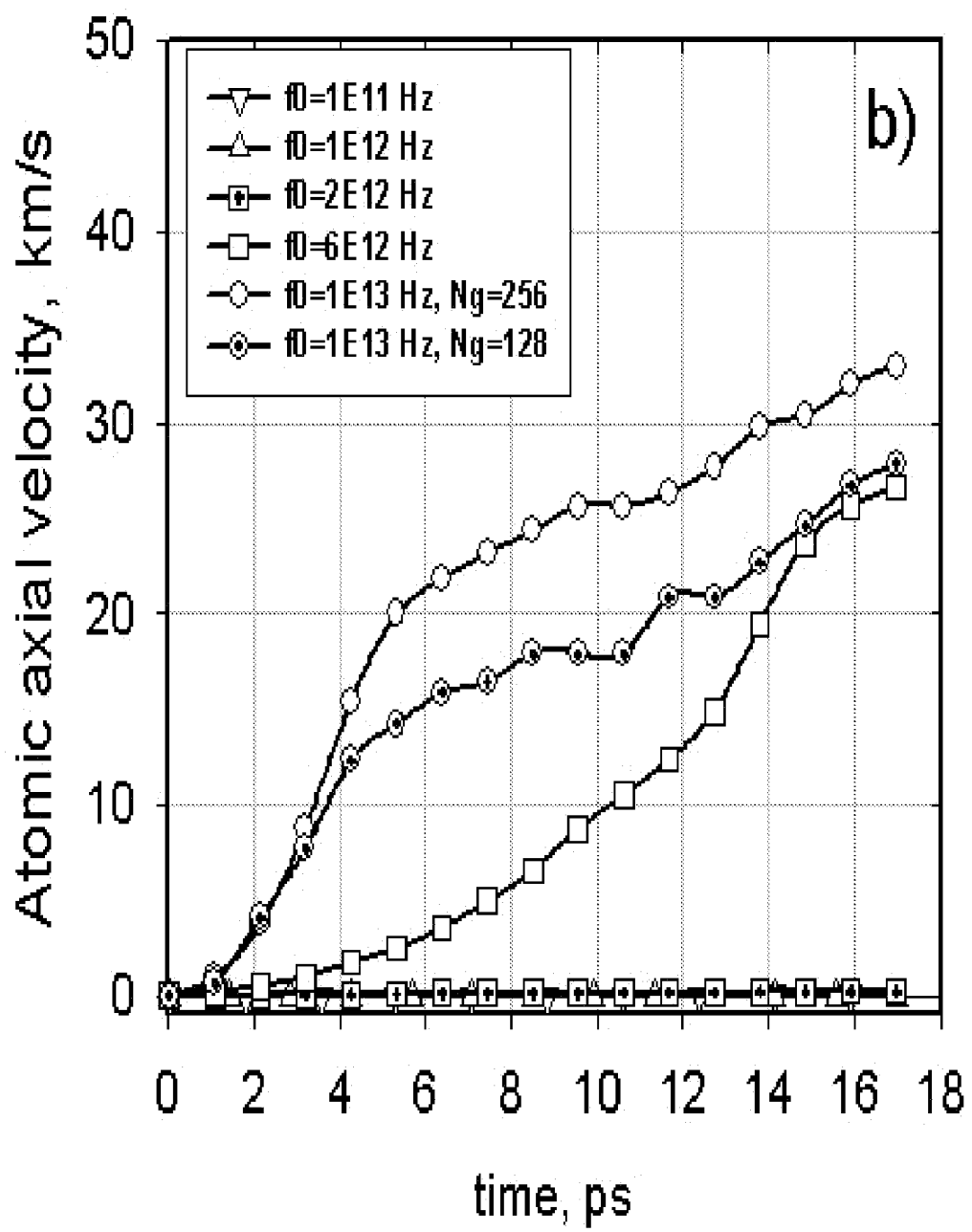

The average axial velocities of helium atoms are shown in FIG. 2B for various wave frequencies. At about 1 THz, the velocity (flow rate) is rather small. However, at 6 THz, the velocity reaches a hyper-thermal value of about 30 km/s (kinetic energy of the atoms is greater than the thermal energy, $k_B T$).

Figure 3A:
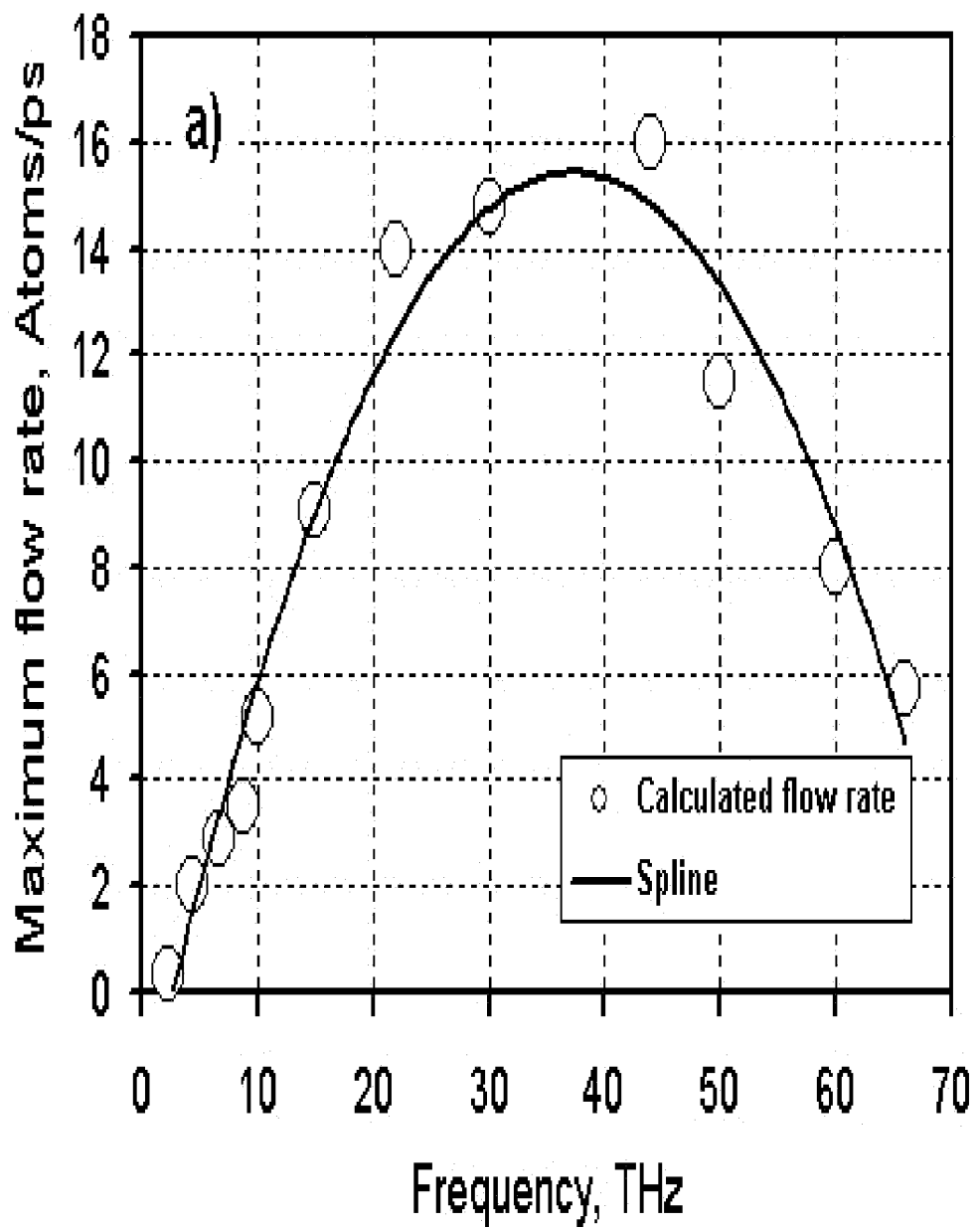
FIGS. 3A-3B are graphs displaying the frequency-dependence of the flow rate of the media through the small scale tubes, in this case nano-tubes.

The frequency dependence of the flow rate is illustrated in FIG. 3A and depends on the total length of the tube. In this particular simulation, the tube length was chosen to be 100 Å (10 nm) and, therefore, the characteristic frequency of the surface wave is very high. The maximum pumping effect (flow rate) is seen at approximately 38 THz. The maximum flow rates (and axial velocities) for a particular tube will occur at different frequencies which depend upon the length of the tube.

Figure 3B:
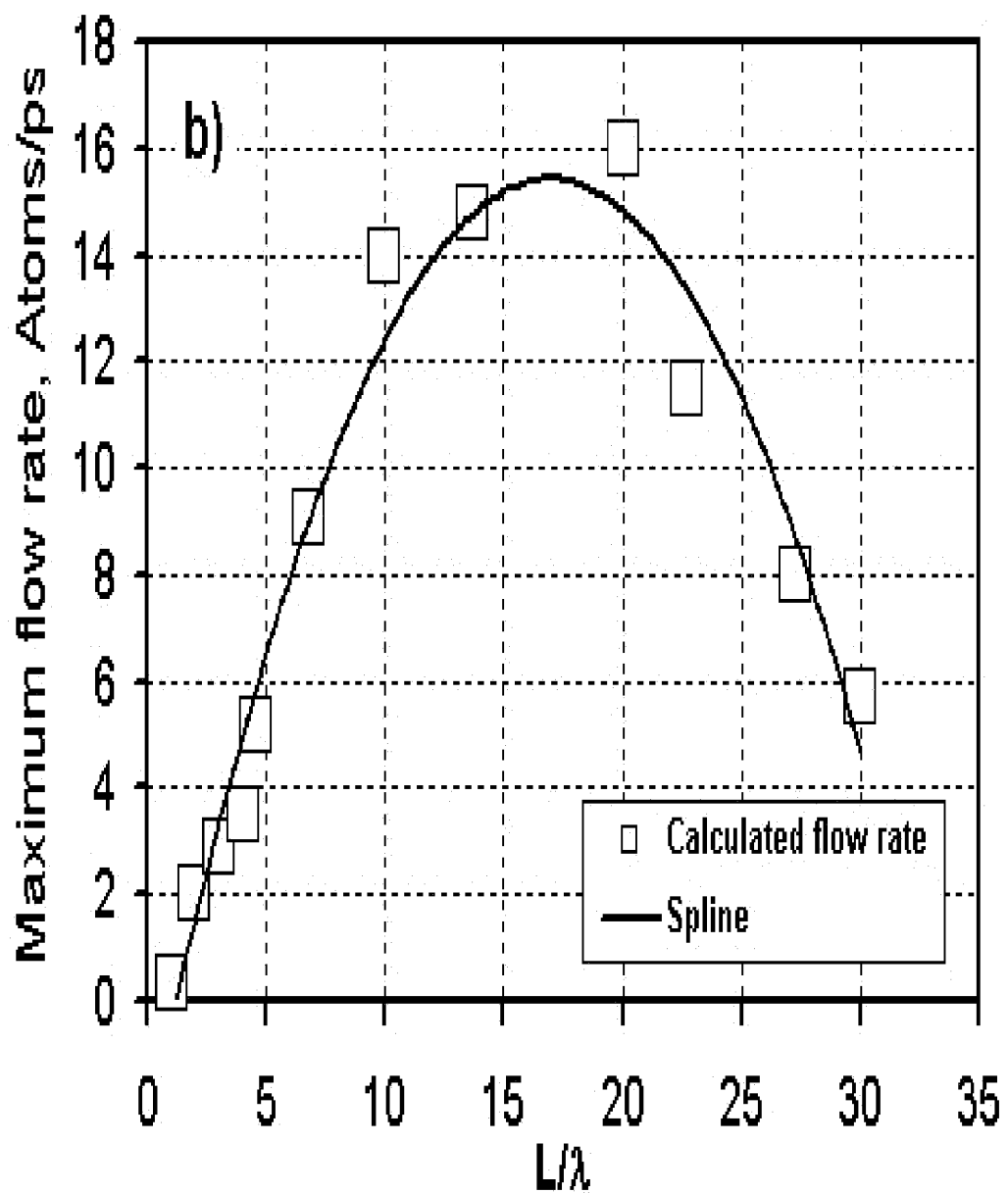

FIG. 3B shows the dependence of the small scale pumping effect (flow rate) on the ratio of L/λ, where L is the tube length and λ is the wavelength of the surface wave. Thus the ratio of L/λ is a salient aspect of one or more embodiments of the invention and a preferred frequency range for a particular nano or micro tube will be dependent upon the tubes length. The ratio between the L and frequency will be between about 2 and 32, more preferably between about 10 and 25 (See, FIG. 3B illustrating the importance of the ratio).

EXAMPLES

The invented small scale pumping method can be used in a myriad of applications ranging from medicine to energy storage. For example, one embodiment of the invention relates to a method of drug delivery, the micro and/or nanotubes could be filled with a medicine and attached to a substrate. The tube device could then be implanted in the body. The medicine could then be released from the tubes by the application, locally, of ultrasound or short laser pulses by a source present on the tube device. Alternatively, the ultrasound or short laser pulses could be applied externally to the body in the location where the tube device has been implanted. The ultrasound or short laser pulses would cause the medicine to be pumped out of the tube. This application could allow for precision drug delivery in the treatment of, for example, cancerous tumors.

Yet another embodiment of the invention relates to the use of nano and/or micro pumping for hydrogen storage. The present invention could provide an efficient means for storing and subsequently releasing hydrogen for use in fuel cells and other uses.

Yet another embodiment of the invention relates to the use micro pumping in direct methanol fuel cells. The present invention could provide an efficient means for storing and subsequently releasing air and fuel for use in fuel cells and other uses.

Another embodiment relates to the use of small scale pumping in nano and/or micro-robotics to provide a means for movement of robots by providing a nano- and/or micro-hydraulics system Having described the basic concept of the invention, it will be apparent to those skilled in the art that the foregoing detailed disclosure is intended to be presented by way of example only, and is not limiting. Various alterations, improvements, and modifications are intended to be suggested and are within the scope and spirit of the present invention. Additionally, the recited order of the elements or sequences, or the use of numbers, letters or other designations therefore, is not intended to limit the claimed processes to any order except as may be specified in the claims. All ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as up to, at least, greater than, less than, and the like refer to ranges which can be subsequently broken down into sub-ranges as discussed above. Accordingly, the invention is limited only by the following claims and equivalents thereto. The invention can be applied and adapted to presently known and future developed methods and system.

All publications and patent documents cited in this application are incorporated by reference in their entirety for all purposes to the same extent as if each individual publication or patent document were so individually denoted.

What is claimed is:

1. A method for small scale pumping, comprising the following steps:
providing one or more media;
providing one or more microtubes, the one or more microtubes having a first end and a second end, wherein said first end of the one or more microtubes is in contact with the one or more media; and
creating surface waves on the one or more microtubes,
wherein at least a portion of the media is pumped through the one or more microtubes, wherein the wherein the one or microtubes has a defined length L, the surface wave has a defined frequency $\lambda$ and wherein the ratio between $L/\lambda$ is between about 2 and 32.

2. The method of claim 1, wherein the one or more media is a liquid, solid, gas or combination thereof.

3. The method of claim 1, wherein the surface waves are Rayleigh transverse surface waves.

4. The method of claim 1, wherein the surface waves are created by sending ultrasound waves to the microtubes.

5. The method of claim 1, wherein the maximum atomic flow rate of the media is between about 0.001 and 45 atoms/ps.

6. The method of claim 1, wherein the maximum atomic axial velocity of the media is between about 0.01 and 35 km/s.

7. The method of claim 1, wherein the microtube has a defined length L, the surface wave has a defined frequency $\lambda$ and wherein the ratio between $L/\lambda$ is between about 10 and 25.

8. The method of claim 1, wherein the microtubes have a diameter of less than about 200 microns.

9. A method for micro-pumping, comprising the following steps:
providing one or more microtubes, each tube having a first end and a second end;
imbibing the one or more microtubes with a media; and
creating surface waves on the one or more microtubes,
wherein the one or more microtubes has a defined length L, the surface wave has a defined frequency $\lambda$ and wherein the ratio between $L/\lambda$ is between about 2 and 32.

10. The method of claim 9, wherein the microtubes are open at both the first and second ends.

11. The method of claim 9, wherein the microtubes are capped at the first end and open at the second end.

12. The method of claim 9, wherein the first end of the one or more microtubes is in contact with the media.

13. The method of claim 9, wherein the media is a liquid, gas, solid or combination thereof.

14. The method of claim 9, wherein the surface waves are created by sending ultrasound waves to the tubes.

15. The method of claim 9, wherein the maximum atomic flow rate of the media is between about 0.001 and 45 atoms/ps.

16. The method of claim 9, wherein the diameter of the one or more microtubes is less than about 200 microns.

17. The method of claim 9, wherein the maximum atomic axial velocity of the media is between about 0.01 and 35 km/s.

18. The method of claim 9, wherein the one or more microtubes has a defined length L, the surface wave has a defined frequency $\lambda$ and wherein the ratio between $L/\lambda$ is between about 10 and 25.

* * * * *